(12) United States Patent
Benschop et al.

(10) Patent No.: US 10,501,536 B2
(45) Date of Patent: Dec. 10, 2019

(54) ANTI-IL-33 ANTIBODIES AND USES THEREOF FOR DISEASE TREATMENT

(71) Applicant: Eli Lilly and Company, Indianapolis, IN (US)

(72) Inventors: Robert Jan Benschop, Indianapolis, IN (US); Julian Davies, La Jolla, CA (US); Angela Jeannine Okragly, Indianapolis, IN (US); Chetankumar Natvarlal Patel, Fishers, IN (US); Stephanie Marie Truhlar, Carlsbad, CA (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 15/791,641

(22) Filed: Oct. 24, 2017

(65) Prior Publication Data

US 2018/0118821 A1    May 3, 2018

Related U.S. Application Data

(60) Provisional application No. 62/414,258, filed on Oct. 28, 2016.

(51) Int. Cl.
| | | |
|---|---|---|
| A61K 39/395 | (2006.01) | |
| C07K 16/24 | (2006.01) | |
| A61P 11/06 | (2006.01) | |
| A61P 17/00 | (2006.01) | |
| A61P 37/08 | (2006.01) | |
| A61P 1/00 | (2006.01) | |
| A61P 11/00 | (2006.01) | |
| A61K 39/00 | (2006.01) | |

(52) U.S. Cl.
CPC .............. *C07K 16/244* (2013.01); *A61P 1/00* (2018.01); *A61P 11/00* (2018.01); *A61P 11/06* (2018.01); *A61P 17/00* (2018.01); *A61P 37/08* (2018.01); *A61K 2039/505* (2013.01); *C07K 2317/34* (2013.01); *C07K 2317/565* (2013.01); *C07K 2317/567* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 9,611,307 B2 | 4/2017 | Girard et al. |
| 9,970,944 B2 | 5/2018 | Schmitz et al. |
| 2014/0271658 A1 | 9/2014 | Murphy et al. |
| 2016/0168242 A1 | 6/2016 | Hass et al. |
| 2016/0289322 A1 | 10/2016 | Fujino et al. |

FOREIGN PATENT DOCUMENTS

| | | |
|---|---|---|
| EP | 1725261 B1 | 1/2011 |
| EP | 2678355 B1 | 8/2016 |
| EP | 2475388 B1 | 11/2017 |
| WO | 2008/132709 A1 | 11/2008 |
| WO | 2008/144610 A1 | 11/2008 |
| WO | 2013/165894 A2 | 11/2013 |
| WO | 2014/164959 A2 | 10/2014 |
| WO | 2015/106080 A2 | 7/2015 |
| WO | 2016/077381 A1 | 5/2016 |
| WO | 2016/156440 A1 | 10/2016 |
| WO | 2017124110 A1 | 7/2017 |

OTHER PUBLICATIONS

Liu X, et al, "Anti-IL-33 antibody treatment inhibits airway inflammation in murine model of allergic asthma", Biochemical and Biophysical Research Communications, Elsevier, Amsterdam, NL, vol. 386, No. 1, available online Jun. 7, 2009.

Kim Y H, et al: "Anti-IL-33 antibody has a therapeutic effect in a murine model of allergic rhinitis", Allergy, Wiley-Blackwell Publishing LTD, United Kingdom, vol. 67, 2012.

Nabe T: "Interleukin (IL)—33: New Therapeutic Target for Atopic Diseases", Journal of Pharmacological Sciences, vol. 126, available online Sep. 10, 2014.

*Primary Examiner* — Dong Jiang
(74) *Attorney, Agent, or Firm* — Megan N Thobe

(57) ABSTRACT

Antibodies which bind and neutralize human IL-33, and methods of using same, are provided, said antibodies are useful as agents for treating conditions associated with allergic disease including treating atopic dermatitis.

17 Claims, No Drawings
Specification includes a Sequence Listing.

SEQUENCE LISTING

<160> NUMBER OF SEQ ID NOS: 21

<210> SEQ ID NO 1
<211> LENGTH: 449
<212> TYPE: PRT
<213> ORGANISM: Artificial Sequence
<220> FEATURE:
<223> OTHER INFORMATION: Synthetic Construct

<400> SEQUENCE: 1

Glu Val Gln Leu Val Glu Thr Gly Gly Gly Leu Ile Gln Pro Gly Gly
1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Leu His Gly Ile Arg Ala Tyr Asp Ala Phe Ile Ile
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

```
Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
                390                 395                 400
385

Leu Asp Ser Asp Gly Ser Phe Phe Leu Tyr Ser Arg Leu Thr Val Asp
            405                 410                 415

Lys Ser Arg Trp Gln Glu Gly Asn Val Phe Ser Cys Ser Val Met His
        420                 425                 430

Glu Ala Leu His Asn His Tyr Thr Gln Lys Ser Leu Ser Leu Ser Leu
    435                 440                 445

Gly

<210> SEQ ID NO 2
<211> LENGTH: 215
<212> TYPE: PRT
<213> ORGANISM: Artificial sequence
<220> FEATURE:
<223> OTHER INFORMATION: Synthetic Construct

<400> SEQUENCE: 2

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ile Asn
            20                  25                  30

Leu Ser Trp Tyr Gln Gln Lys Pro Gly Gln Ala Pro Arg Leu Leu Ile
        35                  40                  45
```

```
Tyr Gly Ala Ser His Arg Ala Thr Gly Ile Pro Asp Arg Phe Ser Gly
        50                  55                  60
Ser Gly Ser Gly Thr Asp Phe Thr Leu Thr Ile Ser Arg Leu Glu Pro
 65                  70                  75                  80
Glu Asp Phe Ala Val Tyr Tyr Cys His Gln Tyr Ser Gln Ser Pro Pro
                 85                  90                  95
Phe Thr Phe Gly Gly Gly Thr Lys Val Glu Ile Lys Arg Thr Val Ala
            100                 105                 110
Ala Pro Ser Val Phe Ile Phe Pro Pro Ser Asp Glu Gln Leu Lys Ser
            115                 120                 125
Gly Thr Ala Ser Val Val Cys Leu Leu Asn Asn Phe Tyr Pro Arg Glu
        130                 135                 140
Ala Lys Val Gln Trp Lys Val Asp Asn Ala Leu Gln Ser Gly Asn Ser
145                 150                 155                 160
Gln Glu Ser Val Thr Glu Gln Asp Ser Lys Asp Ser Thr Tyr Ser Leu
                165                 170                 175
Ser Ser Thr Leu Thr Leu Ser Lys Ala Asp Tyr Glu Lys His Lys Val
            180                 185                 190
Tyr Ala Cys Glu Val Thr His Gln Gly Leu Ser Ser Pro Val Thr Lys
        195                 200                 205
Ser Phe Asn Arg Gly Glu Cys
        210                 215

<210> SEQ ID NO 3
<211> LENGTH: 123
<212> TYPE: PRT
<213> ORGANISM: Artificial sequence
<220> FEATURE:
<223> OTHER INFORMATION: Synthetic Construct

<400> SEQUENCE: 3

Glu Val Gln Leu Val Glu Thr Gly Gly Gly Leu Ile Gln Pro Gly Gly
 1               5                  10                  15
Ser Leu Arg Leu Ser Cys Ala Ala Ser Gly Phe Thr Phe Ser Ser Tyr
             20                  25                  30
Ala Met Ser Trp Val Arg Gln Ala Pro Gly Lys Gly Leu Glu Trp Val
         35                  40                  45
Ser Ala Ile Ser Gly Ser Gly Gly Ser Thr Tyr Tyr Ala Asp Ser Val
     50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Thr Leu His Gly Ile Arg Ala Ala Tyr Asp Ala Phe Ile Ile
            100                 105                 110
Trp Gly Gln Gly Thr Leu Val Thr Val Ser Ser
            115                 120

<210> SEQ ID NO 4
<211> LENGTH: 108
<212> TYPE: PRT
<213> ORGANISM: Artificial sequence
<220> FEATURE:
<223> OTHER INFORMATION: Synthetic Construct
```

<400> SEQUENCE: 4

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ile Asn
            20                  25                  30

Leu Ser Trp Tyr Gln Gln Lys Pro Gly Gln Ala Pro Arg Leu Leu Ile
        35                  40                  45

Tyr Gly Ala Ser His Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys His Gln Tyr Ser Gln Ser Pro Pro
                85                  90                  95

Phe Thr Phe Gly Gly Gly Thr Lys Val Glu Ile Lys
            100                 105
```

<210> SEQ ID NO 5
<211> LENGTH: 449
<212> TYPE: PRT
<213> ORGANISM: Artificial sequence
<220> FEATURE:
<223> OTHER INFORMATION: Synthetic Construct

<400> SEQUENCE: 5

```
Glu Val Gln Leu Val Glu Thr Gly Gly Gly Leu Ile Gln Pro Gly Gly
1               5                   10                  15

Ser Leu Arg Leu Ser Cys Ala Ala Ser Gly Phe Thr Phe Ser Phe Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Leu His Gly Ile Arg Ala Ala Tyr Asp Ala Phe Ile Ile
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Ala Ala Gly Gly
225                 230                 235                 240
```

-continued

```
Pro Ser Val Phe Leu Phe Pro Pro Lys Pro Lys Asp Thr Leu Met Ile
            245                 250                 255

Ser Arg Thr Pro Glu Val Thr Cys Val Val Asp Val Ser Gln Glu
        260                 265                 270

Asp Pro Glu Val Gln Phe Asn Trp Tyr Val Asp Gly Val Glu Val His
    275                 280                 285

Asn Ala Lys Thr Lys Pro Arg Glu Glu Gln Phe Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Gln Glu Glu Met Thr Lys Asn Gln Val Ser Leu
    355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Leu
    435                 440                 445

Gly

<210> SEQ ID NO 6
<211> LENGTH: 215
<212> TYPE: PRT
<213> ORGANISM: Artificial sequence
<220> FEATURE:
<223> OTHER INFORMATION: Synthetic Construct

<400> SEQUENCE: 6

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ile Asn
            20                  25                  30

Leu Ser Trp Tyr Gln Gln Lys Pro Gly Gln Ala Pro Arg Leu Leu Ile
        35                  40                  45

Tyr Gly Ala Ser His Arg Leu Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys His Gln Tyr Ser Gln Pro Pro Pro
                85                  90                  95

Phe Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140
```

```
Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 7
<211> LENGTH: 123
<212> TYPE: PRT
<213> ORGANISM: Artificial sequence
<220> FEATURE:
<223> OTHER INFORMATION: Synthetic Construct

<400> SEQUENCE: 7

Glu Val Gln Leu Val Glu Thr Gly Gly Gly Leu Ile Gln Pro Gly Gly
1               5                   10                  15

Ser Leu Arg Leu Ser Cys Ala Ala Ser Gly Phe Thr Phe Ser Phe Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Leu His Gly Ile Arg Ala Ala Tyr Asp Ala Phe Ile Ile
            100                 105                 110

Trp Gly Gln Gly Thr Leu Val Thr Val Ser Ser
        115                 120

<210> SEQ ID NO 8
<211> LENGTH: 108
<212> TYPE: PRT
<213> ORGANISM: Artificial sequence
<220> FEATURE:
<223> OTHER INFORMATION: Synthetic Construct

<400> SEQUENCE: 8

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ile Asn
            20                  25                  30

Leu Ser Trp Tyr Gln Gln Lys Pro Gly Gln Ala Pro Arg Leu Leu Ile
        35                  40                  45

Tyr Gly Ala Ser His Arg Leu Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys His Gln Tyr Ser Gln Pro Pro Pro
                85                  90                  95

Phe Thr Phe Gly Gly Gly Thr Lys Val Glu Ile Lys
            100                 105
```

```
<210> SEQ ID NO 9
<211> LENGTH: 449
<212> TYPE: PRT
<213> ORGANISM: Artificial sequence
<220> FEATURE:
<223> OTHER INFORMATION: Synthetic Construct

<400> SEQUENCE: 9
```

| | | | | | | | | | | | | | | | |
|---|---|---|---|---|---|---|---|---|---|---|---|---|---|---|---|
| Glu | Val | Gln | Leu | Val | Glu | Thr | Gly | Gly | Gly | Leu | Ile | Gln | Pro | Gly | Gly |
| 1 | | | | 5 | | | | | 10 | | | | | 15 | |
| Ser | Leu | Arg | Leu | Ser | Cys | Ala | Ala | Ser | Gly | Phe | Thr | Phe | Ser | Phe | Tyr |
| | | | 20 | | | | | 25 | | | | | 30 | | |
| Ala | Met | Ser | Trp | Val | Arg | Gln | Ala | Pro | Gly | Lys | Gly | Leu | Glu | Trp | Val |
| | | 35 | | | | | 40 | | | | | 45 | | | |
| Ser | Ala | Ile | Ser | Gly | Ser | Gly | Gly | Ser | Thr | Tyr | Tyr | Ala | Asp | Ser | Val |
| | 50 | | | | | 55 | | | | | 60 | | | | |
| Lys | Gly | Arg | Phe | Thr | Ile | Ser | Arg | Asp | Asn | Ser | Lys | Asn | Thr | Leu | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Ala | Arg | Thr | Ile | His | Gly | Ile | Arg | Ala | Ala | Tyr | Asp | Ala | Phe | Ile | Ile |
| | | | 100 | | | | | 105 | | | | | 110 | | |
| Trp | Gly | Gln | Gly | Thr | Leu | Val | Thr | Val | Ser | Ser | Ala | Ser | Thr | Lys | Gly |
| | | 115 | | | | | 120 | | | | | 125 | | | |
| Pro | Ser | Val | Phe | Pro | Leu | Ala | Pro | Cys | Ser | Arg | Ser | Thr | Ser | Glu | Ser |
| | 130 | | | | | 135 | | | | | 140 | | | | |
| Thr | Ala | Ala | Leu | Gly | Cys | Leu | Val | Lys | Asp | Tyr | Phe | Pro | Glu | Pro | Val |
| 145 | | | | | 150 | | | | | 155 | | | | | 160 |
| Thr | Val | Ser | Trp | Asn | Ser | Gly | Ala | Leu | Thr | Ser | Gly | Val | His | Thr | Phe |
| | | | | 165 | | | | | 170 | | | | | 175 | |
| Pro | Ala | Val | Leu | Gln | Ser | Ser | Gly | Leu | Tyr | Ser | Leu | Ser | Ser | Val | Val |
| | | | 180 | | | | | 185 | | | | | 190 | | |
| Thr | Val | Pro | Ser | Ser | Ser | Leu | Gly | Thr | Lys | Thr | Tyr | Thr | Cys | Asn | Val |
| | | 195 | | | | | 200 | | | | | 205 | | | |
| Asp | His | Lys | Pro | Ser | Asn | Thr | Lys | Val | Asp | Lys | Arg | Val | Glu | Ser | Lys |
| | 210 | | | | | 215 | | | | | 220 | | | | |
| Tyr | Gly | Pro | Pro | Cys | Pro | Pro | Cys | Pro | Ala | Pro | Glu | Ala | Ala | Gly | Gly |
| 225 | | | | | 230 | | | | | 235 | | | | | 240 |
| Pro | Ser | Val | Phe | Leu | Phe | Pro | Pro | Lys | Pro | Lys | Asp | Thr | Leu | Met | Ile |
| | | | | 245 | | | | | 250 | | | | | 255 | |
| Ser | Arg | Thr | Pro | Glu | Val | Thr | Cys | Val | Val | Val | Asp | Val | Ser | Gln | Glu |
| | | | 260 | | | | | 265 | | | | | 270 | | |
| Asp | Pro | Glu | Val | Gln | Phe | Asn | Trp | Tyr | Val | Asp | Gly | Val | Glu | Val | His |
| | | 275 | | | | | 280 | | | | | 285 | | | |
| Asn | Ala | Lys | Thr | Lys | Pro | Arg | Glu | Glu | Gln | Phe | Asn | Ser | Thr | Tyr | Arg |
| | 290 | | | | | 295 | | | | | 300 | | | | |
| Val | Val | Ser | Val | Leu | Thr | Val | Leu | His | Gln | Asp | Trp | Leu | Asn | Gly | Lys |
| 305 | | | | | 310 | | | | | 315 | | | | | 320 |
| Glu | Tyr | Lys | Cys | Lys | Val | Ser | Asn | Lys | Gly | Leu | Pro | Ser | Ser | Ile | Glu |
| | | | | 325 | | | | | 330 | | | | | 335 | |
| Lys | Thr | Ile | Ser | Lys | Ala | Lys | Gly | Gln | Pro | Arg | Glu | Pro | Gln | Val | Tyr |
| | | | 340 | | | | | 345 | | | | | 350 | | |
| Thr | Leu | Pro | Pro | Ser | Gln | Glu | Glu | Met | Thr | Lys | Asn | Gln | Val | Ser | Leu |
| | | 355 | | | | | 360 | | | | | 365 | | | |

-continued

```
Thr Cys Leu Val Lys Gly Phe Tyr Pro Ser Asp Ile Ala Val Glu Trp
            370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Arg Leu Thr Val Asp
                405                 410                 415
Lys Ser Arg Trp Gln Glu Gly Asn Val Phe Ser Cys Ser Val Met His
                420                 425                 430
Glu Ala Leu His Asn His Tyr Thr Gln Lys Ser Leu Ser Leu Ser Leu
                435                 440                 445
Gly

<210> SEQ ID NO 10
<211> LENGTH: 215
<212> TYPE: PRT
<213> ORGANISM: Artificial sequence
<220> FEATURE:
<223> OTHER INFORMATION: Synthetic Construct

<400> SEQUENCE: 10

Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Gly Ile Asn
                20                  25                  30
Leu Ser Trp Tyr Gln Gln Lys Pro Gly Gln Ala Pro Arg Leu Leu Ile
            35                  40                  45
Tyr Gly Ala Ser His Arg Leu Thr Gly Ile Pro Asp Arg Phe Ser Gly
    50                  55                  60
Ser Gly Ser Gly Thr Asp Phe Thr Leu Thr Ile Ser Arg Leu Glu Pro
65                  70                  75                  80
Glu Asp Phe Ala Val Tyr Tyr Cys His Gln Tyr Ser Gln Pro Pro Pro
                85                  90                  95
Phe Thr Phe Gly Gly Gly Thr Lys Val Glu Ile Lys Arg Thr Val Ala
            100                 105                 110
Ala Pro Ser Val Phe Ile Phe Pro Pro Ser Asp Glu Gln Leu Lys Ser
        115                 120                 125
Gly Thr Ala Ser Val Val Cys Leu Leu Asn Asn Phe Tyr Pro Arg Glu
    130                 135                 140
Ala Lys Val Gln Trp Lys Val Asp Asn Ala Leu Gln Ser Gly Asn Ser
145                 150                 155                 160
Gln Glu Ser Val Thr Glu Gln Asp Ser Lys Asp Ser Thr Tyr Ser Leu
                165                 170                 175
Ser Ser Thr Leu Thr Leu Ser Lys Ala Asp Tyr Glu Lys His Lys Val
            180                 185                 190
Tyr Ala Cys Glu Val Thr His Gln Gly Leu Ser Ser Pro Val Thr Lys
        195                 200                 205
Ser Phe Asn Arg Gly Glu Cys
    210                 215

<210> SEQ ID NO 11
<211> LENGTH: 123
<212> TYPE: PRT
<213> ORGANISM: Artificial sequence
<220> FEATURE:
<223> OTHER INFORMATION: Synthetic Construct
```

<400> SEQUENCE: 11

Glu Val Gln Leu Val Glu Thr Gly Gly Gly Leu Ile Gln Pro Gly Gly
1               5                   10                  15

Ser Leu Arg Leu Ser Cys Ala Ala Ser Gly Phe Thr Phe Ser Phe Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Ile His Gly Ile Arg Ala Ala Tyr Asp Ala Phe Ile Ile
            100                 105                 110

Trp Gly Gln Gly Thr Leu Val Thr Val Ser Ser
        115                 120

<210> SEQ ID NO 12
<211> LENGTH: 108
<212> TYPE: PRT
<213> ORGANISM: Artificial sequence
<220> FEATURE:
<223> OTHER INFORMATION: Synthetic Construct

<400> SEQUENCE: 12

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ile Asn
            20                  25                  30

Leu Ser Trp Tyr Gln Gln Lys Pro Gly Gln Ala Pro Arg Leu Leu Ile
        35                  40                  45

Tyr Gly Ala Ser His Arg Leu Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys His Gln Tyr Ser Gln Pro Pro Pro
                85                  90                  95

Phe Thr Phe Gly Gly Gly Thr Lys Val Glu Ile Lys
            100                 105

<210> SEQ ID NO 13
<211> LENGTH: 10
<212> TYPE: PRT
<213> ORGANISM: Artificial sequence
<220> FEATURE:
<223> OTHER INFORMATION: Synthetic Construct
<220> FEATURE:
<221> NAME/KEY: MISC_FEATURE
<222> LOCATION: (6)..(6)
<223> OTHER INFORMATION: Xaa at position 6 is Ser or Phe

<400> SEQUENCE: 13

Gly Phe Thr Phe Ser Xaa Tyr Ala Met Ser
1               5                   10

<210> SEQ ID NO 14
<211> LENGTH: 17
<212> TYPE: PRT
<213> ORGANISM: Artificial sequence

```
<220> FEATURE:
<223> OTHER INFORMATION: Synthetic Construct

<400> SEQUENCE: 14

Ala Ile Ser Gly Ser Gly Gly Ser Thr Tyr Tyr Ala Asp Ser Val Lys
1               5                   10                  15

Gly

<210> SEQ ID NO 15
<211> LENGTH: 14
<212> TYPE: PRT
<213> ORGANISM: Artificial sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Leu or Ile

<400> SEQUENCE: 15

Thr Xaa His Gly Ile Arg Ala Ala Tyr Asp Ala Phe Ile Ile
1               5                   10

<210> SEQ ID NO 16
<211> LENGTH: 11
<212> TYPE: PRT
<213> ORGANISM: Artificial sequence
<220> FEATURE:
<223> OTHER INFORMATION: Synthetic Construct

<400> SEQUENCE: 16

Arg Ala Ser Gln Ser Val Gly Ile Asn Leu Ser
1               5                   10

<210> SEQ ID NO 17
<211> LENGTH: 7
<212> TYPE: PRT
<213> ORGANISM: Artificial sequence
<220> FEATURE:
<223> OTHER INFORMATION: Synthetic Construct
<220> FEATURE:
<221> NAME/KEY: MISC_FEATURE
<222> LOCATION: (6)..(6)
<223> OTHER INFORMATION: Xaa at position 6 is Ala or Leu

<400> SEQUENCE: 17

Gly Ala Ser His Arg Xaa Thr
1               5

<210> SEQ ID NO 18
<211> LENGTH: 10
<212> TYPE: PRT
<213> ORGANISM: Artificial sequence
<220> FEATURE:
<223> OTHER INFORMATION: Synthetic Construct
<220> FEATURE:
<221> NAME/KEY: MISC_FEATURE
<222> LOCATION: (6)..(6)
<223> OTHER INFORMATION: Xaa at position 6 is Ser or Pro

<400> SEQUENCE: 18

His Gln Tyr Ser Gln Xaa Pro Pro Phe Thr
1               5                   10

<210> SEQ ID NO 19
<211> LENGTH: 176
<212> TYPE: PRT
<213> ORGANISM: Homo Sapiens
```

<400> SEQUENCE: 19

Ala Phe Gly Ile Ser Gly Val Gln Lys Tyr Thr Arg Ala Leu His Asp
1               5                   10                  15

Ser Ser Ile Thr Gly Ile Ser Pro Ile Thr Glu Tyr Leu Ala Ser Leu
            20                  25                  30

Ser Thr Tyr Asn Asp Gln Ser Ile Thr Phe Ala Leu Glu Asp Glu Ser
        35                  40                  45

Tyr Glu Ile Tyr Val Glu Asp Leu Lys Lys Asp Glu Lys Lys Asp Lys
    50                  55                  60

Val Leu Leu Ser Tyr Tyr Glu Ser Gln His Pro Ser Asn Glu Ser Gly
65                  70                  75                  80

Asp Gly Val Asp Gly Lys Met Leu Met Val Thr Leu Ser Pro Thr Lys
                85                  90                  95

Asp Phe Trp Leu His Ala Asn Asn Lys Glu His Ser Val Glu Leu His
            100                 105                 110

Lys Cys Glu Lys Pro Leu Pro Asp Gln Ala Phe Phe Val Leu His Asn
        115                 120                 125

Met His Ser Asn Cys Val Ser Phe Glu Cys Lys Thr Asp Pro Gly Val
    130                 135                 140

Phe Ile Gly Val Lys Asp Asn His Leu Ala Leu Ile Lys Val Asp Ser
145                 150                 155                 160

Ser Glu Asn Leu Cys Thr Glu Asn Ile Leu Phe Lys Leu Ser Glu Thr
                165                 170                 175

<210> SEQ ID NO 20
<211> LENGTH: 1347
<212> TYPE: DNA
<213> ORGANISM: Artificial sequence
<220> FEATURE:
<223> OTHER INFORMATION: Synthetic Construct

<400> SEQUENCE: 20
gaggtgcagc tggtggagac tggaggaggc ttgatccagc ctggggggtc cctgagactc      60
tcctgtgcag cctctggatt caccttagc ttttatgcta tgagctgggt ccgccaggct     120
ccagggaagg ggctggagtg ggtctcagct attagtggta gtggtggtag cacatactac     180
gcagattccg tgaagggccg attcaccatc tccagagaca attccaagaa cacgctgtat     240
cttcaaatga acagcctgag agccgaggac acggccgtgt attactgtgc agaaacgatc     300
cacggtatac gcgcagccta tgatgctttt attatctggg gccagggcac cctggtcacc     360
gtctcctcag cttctaccaa gggcccatcg gtcttccccg tagcgccctg ctccaggagc     420
acctccgaga gcacagccgc cctgggctgc ctggtcaagg actacttccc cgaaccggtg     480
acggtgtcgt ggaactcagg cgccctgacc agcggcgtgc acaccttccc ggctgtccta     540
cagtcctcag gactctactc cctcagcagc gtggtgaccg tgccctccag cagcttgggc     600
acgaagacct acacctgcaa cgtagatcac aagcccagca acaccaaggt ggacaagaga     660
gttgagtcca aatatggtcc cccatgccca ccctgcccag cacctgaggc cgccggggga     720
ccatcagtct tcctgttccc cccaaaaccc aaggacactc tcatgatctc ccggaccct      780 gaggtcacgt gcgtggtggt ggacgtgagc caggaagacc ccgaggtcca gttcaactgg     840
tacgtggatg gcgtggaggt gcataatgcc aagacaaagc cgcgggagga gcagttcaac     900
agcacgtacc gtgtggtcag cgtcctcacc gtcctgcacc aggactggct gaacggcaag     960
gagtacaagt gcaaggtctc caacaaaggc ctcccgtcct ccatcgagaa aaccatctcc    1020

-continued

```
aaagccaaag  ggcagccccg  agagccacag  gtgtacaccc  tgcccccatc  ccaggaggag   1080
atgaccaaga  accaggtcag  cctgacctgc  ctggtcaaag  gcttctaccc  cagcgacatc   1140
gccgtggagt  gggaaagcaa  tgggcagccg  gagaacaact  acaagaccac  gcctcccgtg   1200
ctggactccg  acggctcctt  cttcctctac  agcaggctaa  ccgtggacaa  gagcaggtgg   1260
caggagggga  atgtcttctc  atgctccgtg  atgcatgagg  ctctgcacaa  ccactacaca   1320
cagaagagcc  tctccctgtc  tctgggt                                         1347

<210> SEQ ID NO 21
<211> LENGTH: 645
<212> TYPE: DNA
<213> ORGANISM: Artificial sequence
<220> FEATURE:
<223> OTHER INFORMATION: Synthetic Construct

<400> SEQUENCE: 21
gaaattgtgt  tgacgcagtc  tccaggcacc  ctgtctttgt  ctccagggga  aagagccacc     60
ctctcctgca  gggccagtca  gagtgttggc  atcaacttgt  cctggtacca  gcagaaacct    120
ggccaggctc  ccaggctcct  catctatggt  gcatcccata  ggctaactgg  catcccagac    180
aggttcagtg  gcagtgggtc  tgggacagac  ttcactctca  ccatcagcag  actggagcct    240
gaagattttg  cagtgtatta  ctgtcatcaa  tatagtcaac  cacctcccct  cactttcggc    300
ggagggacca  aggtggagat  caaacggacc  gtggctgcac  catctgtctt  catcttcccg    360
ccatctgatg  agcagttgaa  atctggaact  gcctctgttg  tgtgcctgct  gaataacttc    420
tatcccagag  aggccaaagt  acagtggaag  gtggataacg  ccctccaatc  gggtaactcc    480
caggagagtg  tcacagagca  ggacagcaag  gacagcacct  acagcctcag  cagcaccctg    540
acgctgagca  aagcagacta  cgagaaacac  aaagtctacg  cctgcgaagt  cacccatcag    600
ggcctgagct  cgcccgtcac  aaagagcttc  aacaggggag  agtgc                    645
```

1

ANTI-IL-33 ANTIBODIES AND USES THEREOF FOR DISEASE TREATMENT

The present invention is in the field of medicine. More particularly, the present invention relates to antibodies directed against interleukin-33 (IL-33) and pharmaceutical compositions thereof. The antibodies of the present invention are expected to be useful in the treatment of atopic dermatitis.

Atopic dermatitis (also known as atopic eczema) is a chronic inflammatory allergic skin disease that is characterized by recurrent red, itchy lesions. Two major pathophysiological abnormalities are observed in atopic dermatitis patients; cutaneous inflammation due to inappropriate immune responses in the skin and altered epidermal structure and function. The inflammatory infiltrate is comprised of a mixture of cells, in particular immune cells expressing IL-4, IL-5 and IL-13. These cytokines are often elevated in other allergic diseases including asthma and allergic rhinitis.

Atopic dermatitis has been described as the leading non-fatal health burden attributable to skin diseases. Although it most often starts in infancy and affects two out of ten children, it is also highly prevalent in adults. Most adults who suffer from chronic atopic dermatitis have had nearly lifelong disease. Itch, sleep deprivation, and social embarrassment due to visible lesions have substantial effects on the psychosocial wellbeing of patients and their relatives. In children, the effect of atopic dermatitis on health-related quality of life is similar to that of other major childhood disorders, such as asthma and diabetes. Most people who have atopic dermatitis have a personal or family history of allergies.

Currently, atopic dermatitis cannot be cured, and the aim of disease management is to control or improve symptoms and achieve long-term disease control with a multistep approach. The main principles are continuous epidermal barrier repair with emollients, avoidance of individual trigger factors, and anti-inflammatory therapy with topical corticosteroids or calcineurin inhibitors. In severely affected cases, phototherapy or systemic immunosuppressants are indicated. Hence, there is a need for additional efficacious therapies for patients with atopic dermatitis.

IL-33 is a member of the IL-1 cytokine superfamily, and is mainly expressed by keratinocytes, epithelial cells, and endothelial cells. IL-33 activates several types of innate and acquired immune cells causing the production of other pro-inflammatory mediators, and it is most frequently characterized as an epithelial cytokine that promotes type 2 or T helper 2 (Th2) immune responses. There are a number of antibodies that bind to and neutralize IL-33 known in the art. For example, United States Publication No. 20160168242A1 and International Publication No. WO2015/106080A2 disclose certain antibodies that bind human IL-33. However, there is a need for alternative antibodies that bind human IL-33 with high affinity and are therapeutically effective in treating allergic diseases such as atopic dermatitis. Improved affinity and superior $IC_{50}$ may enable dosing benefits.

The present invention addresses the need for an alternative antibody therapy for patients having allergic diseases such as atopic dermatitis, food allergy, allergic rhinitis, and asthma. In some embodiments, the allergic disease is atopic dermatitis. The present invention also addresses the need for an alternative antibody therapy for patients having persistent inflammatory diseases including eosinophilic esophagitis, scleroderma/systemic sclerosis, ulcerative colitis, and chronic obstructive pulmonary disease. The present invention also addresses the need for an alternative antibody therapy for patients having Crohn's disease.

The present invention provides antibodies that bind human IL-33. In some embodiments, the antibody comprises a light chain variable region (LCVR) and a heavy chain variable region (HCVR), wherein the LCVR comprises complementarity determining regions (CDRs) LCDR1, LCDR2, and LCDR3 and the HCVR comprises CDRs HCDR1, HCDR2, and HCDR3, and wherein the amino acid sequence of LCDR1 is SEQ ID NO: 16, the amino acid sequence of LCDR2 is SEQ ID NO: 17, the amino acid sequence of LCDR3 is SEQ ID NO: 18, the amino acid sequence of HCDR1 is SEQ ID NO: 13, the amino acid sequence of HCDR2 is SEQ ID NO: 14, and the amino acid sequence of HCDR3 is SEQ ID NO: 15. In some such embodiments, Xaa at position 6 of SEQ ID NO: 13 is Ser, Xaa at position 2 of SEQ ID NO: 15 is Leu, Xaa at position 6 of SEQ ID NO: 17 is ala, and Xaa at position 6 of SEQ ID NO: 18 is Ser. In other such embodiments, Xaa at position 6 of SEQ ID NO: 13 is Phe, Xaa at position 2 of SEQ ID NO: 15 is Leu, Xaa at position 6 of SEQ ID NO: 17 is Leu, and Xaa at position 6 of SEQ ID NO: 18 is Pro. In other such embodiments, Xaa at position 6 of SEQ ID NO: 13 is Phe, Xaa at position 2 of SEQ ID NO: 15 is Ile, Xaa at position 6 of SEQ ID NO: 17 is Leu, and Xaa at position 6 of SEQ ID NO: 18 is Pro.

The present invention also provides an antibody that binds human IL-33, wherein the antibody comprises a LCVR and a HCVR, and wherein the amino acid sequence of the LCVR is SEQ ID NO: 4, SEQ ID NO: 8, or SEQ ID NO: 12, and the amino acid sequence of the HCVR is SEQ ID NO: 3, SEQ ID NO: 7, or SEQ ID NO: 11. In a particular embodiment, the amino acid sequence of the LCVR is SEQ ID NO: 4, and the amino acid sequence of the HCVR is SEQ ID NO: 3. In another particular embodiment, the amino acid sequence of the LCVR is SEQ ID NO: 8, and the amino acid sequence of the HCVR is SEQ ID NO: 7. In another particular embodiment, the amino acid sequence of the LCVR is SEQ ID NO: 12, and the amino acid sequence of the HCVR is SEQ ID NO: 11.

The present invention also provides an antibody that binds human IL-33, wherein the antibody comprises a light chain (LC) and a heavy chain (HC), and wherein the amino acid sequence of the LC is SEQ ID NO: 2, SEQ ID NO: 6, or SEQ ID NO: 10, and the amino acid sequence of the HC is SEQ ID NO: 1, SEQ ID NO: 5, or SEQ ID NO: 9. In a particular embodiment, the amino acid sequence of the LC is SEQ ID NO: 2, and the amino acid sequence of the HC is SEQ ID NO: 1. In another particular embodiment, the amino acid sequence of the LC is SEQ ID NO: 6, and the amino acid sequence of the HC is SEQ ID NO: 5. In another particular embodiment, the amino acid sequence of the LC is SEQ ID NO: 10, and the amino acid sequence of the HC is SEQ ID NO: 9.

The present invention also provides an antibody that binds human IL-33, wherein the antibody comprises 2 LCs and 2 HCs, and wherein amino acid sequence of each LC is SEQ ID NO: 2, SEQ ID NO: 6, or SEQ ID NO: 10, and the amino acid sequence of each HC is SEQ ID NO: 1, SEQ ID NO: 5, or SEQ ID NO: 9. In a particular embodiment, the amino acid sequence of each LC is SEQ ID NO: 2, and the amino acid sequence of each HC is SEQ ID NO: 1. In a particular embodiment, the amino acid sequence of each LC is SEQ ID NO: 6, and the amino acid sequence of each HC is SEQ ID NO: 5. In another particular embodiment, the amino acid sequence of each LC is SEQ ID NO: 10, and the amino acid sequence of each HC is SEQ ID NO: 9.

The present invention also provides a pharmaceutical composition comprising an antibody of the present invention, and one or more pharmaceutically acceptable carriers, diluents, or excipients. In some embodiments, pharmaceutical compositions of the present invention can be used in the treatment of an allergic disease, whereby such treatment comprises administering to a patient in need thereof an effective amount of a pharmaceutical composition of the present invention. In some particular embodiments, the allergic disease is atopic dermatitis, asthma, allergic rhinitis, or food allergy. In some embodiments, pharmaceutical compositions of the present invention can be used in the treatment of eosinophilic esophagitis, scleroderma/systemic sclerosis, ulcerative colitis, or chronic obstructive pulmonary disease. In some embodiments, pharmaceutical compositions of the present invention can be used in the treatment of Crohn's disease.

The present invention also provides a method of treating an allergic disease, comprising administering to a patient in need thereof an effective amount of an antibody of the present invention. In some such embodiments, the allergic disease is atopic dermatitis. In other such embodiments, the allergic disease is asthma. In other such embodiments, the allergic disease is food allergy. In other such embodiments, the allergic disease is allergic rhinitis. The present invention also provides a method of treating atopic dermatitis, comprising administering to a patient in need thereof an effective amount of an antibody of the present invention. In some embodiments, the present invention also provides a method of treating at least one of eosinophilic esophagitis, scleroderma/systemic sclerosis, ulcerative colitis, and chronic obstructive pulmonary disease, comprising administering to a patient in need thereof an effective amount of an antibody of the present invention. In some embodiments, the present invention also provides a method of treating Crohn's disease.

The present invention also provides an antibody of the present invention or pharmaceutical composition thereof for use in therapy. In some embodiments, the present invention provides an antibody of the present invention or pharmaceutical composition thereof for use in the treatment of allergic disease, wherein the allergic disease is atopic dermatitis, asthma, allergic rhinitis, or food allergy. In a particular embodiment, the present invention provides an antibody of the present invention or pharmaceutical composition thereof for use in the treatment of atopic dermatitis. In some embodiments, the present invention provides an antibody of the present invention or pharmaceutical composition thereof for use in the treatment of eosinophilic esophagitis, scleroderma/systemic sclerosis, ulcerative colitis, or chronic obstructive pulmonary disease. In some embodiments, the present invention provides an antibody of the present invention or pharmaceutical composition thereof for use in the treatment of Crohn's disease.

In an embodiment, the present invention also provides the use of an antibody of the present invention or a pharmaceutical composition thereof in the manufacture of a medicament for the treatment of allergic disease. In some embodiments, the present invention provides the use of an antibody of the present invention or a pharmaceutical composition thereof in the manufacture of a medicament for the treatment of allergic disease, wherein the allergic disease is atopic dermatitis, asthma, allergic rhinitis, or food allergy. In a particular embodiment, the present invention provides the use of an antibody of the present invention in the manufacture of a medicament for the treatment of atopic dermatitis. In some embodiments, the present invention provides the use of an antibody of the present invention or a pharmaceutical composition thereof in the manufacture of a medicament for the treatment of eosinophilic esophagitis, scleroderma/systemic sclerosis, ulcerative colitis, or chronic obstructive pulmonary disease. In some embodiments, the present invention provides the use of an antibody of the present invention or a pharmaceutical composition thereof in the manufacture of a medicament for the treatment of Crohn's disease.

The present invention also relates to the nucleic acid molecules encoding the antibodies of the present invention. In an embodiment, the present invention provides a DNA molecule comprising a polynucleotide sequence encoding a HC, wherein the amino acid sequence of the HC is SEQ ID NO: 9. According to some such embodiments, the DNA molecule has a polynucleotide sequence given by SEQ ID NO: 20.

In an embodiment, the present invention provides a DNA molecule comprising a polynucleotide sequence encoding a LC, wherein the amino acid sequence of the LC is SEQ ID NO: 10. According to some such embodiments, the DNA molecule has a polynucleotide sequence given by SEQ ID NO: 21.

In a further embodiment, the present invention provides a DNA molecule comprising a polynucleotide sequence encoding a HC having the amino acid sequence of SEQ ID NO: 9, and comprising a polynucleotide sequence encoding a LC having the amino acid sequence of SEQ ID NO: 10. In a particular embodiment, the polynucleotide sequence encoding the HC having the amino acid sequence of SEQ ID NO: 9 is given by SEQ ID NO: 20, and the polynucleotide sequence encoding the LC having the amino acid sequence of SEQ ID NO: 10 is given by SEQ ID NO: 21.

The present invention also provides a mammalian cell transformed with DNA molecule(s), which cell is capable of expressing a compound comprising a HC and a LC of the present invention, wherein the HC is given by SEQ ID NO: 9, and the LC is given by SEQ ID NO: 10. Also, the present invention provides a process for producing a compound comprising the HC and the LC, comprising cultivating the mammalian cell under conditions such that the antibody of the present invention is expressed. The present invention also provides an antibody produced by said process.

In another embodiment, the present invention provides an antibody that contacts human IL-33 at a novel epitope, wherein the epitope has the following residues of SEQ ID NO: 19: Ser at position 23; Pro at position 24; Ile at position 25; Thr at position 26; Glu at position 27; Tyr at position 28; Leu at position 29; Tyr at position 69; Glu at position 71; Val at position 83; Asp at position 84; Lys at position 86; Leu at position 88; Leu at position 126; Asn at position 128; Met at position 129; Asn at position 132; Cys at position 133; Val at position 134; Glu at position 175; and Thr at position 176. In such an embodiment, the epitope is determined by X-ray crystallography where any residue on IL-33 within 4.5 Å of another residue on the bound Fab is considered to be a contact site. The term "epitope" as used herein thus refers to sites of an antigen that are in contact with the variable region of an antibody.

As used herein, an "antibody" is an immunoglobulin molecule comprising 2 HCs and 2 LCs interconnected by disulfide bonds. The amino terminal portion of each LC and HC includes a variable region of about 100-120 amino acids primarily responsible for antigen recognition via the CDRs contained therein. The CDRs are interspersed with regions that are more conserved, termed framework regions ("FR"). Each LCVR and HCVR is composed of 3 CDRs and 4 FRs, arranged from amino-terminus to carboxy-terminus in the following order: FR1, CDR1, FR2, CDR2, FR3, CDR3, FR4. The 3 CDRs of the LC are referred to as "LCDR1, LCDR2, and LCDR3," and the 3 CDRs of the HC are referred to as "HCDR1, HCDR2, and HCDR3." The CDRs contain most of the residues which form specific interactions with the antigen. That is, the CDRs contain most of the residues that are in contact with (within 4.5 Å) the antigen's residues. The functional ability of an antibody to bind a particular antigen is, thus, largely influenced by the amino acid residues within the six CDRs. Assignment of amino acids to CDR domains within the LCVR and HCVR regions of the antibodies of the present invention is based on the well-known Kabat numbering convention (Kabat, et al., Ann. NY Acad. Sci. 190:382-93 (1971); Kabat et al., Sequences of Proteins of Immunological Interest, Fifth Edition, U.S. Department of Health and Human Services, NIH Publication No. 91-3242 (1991)), North numbering convention (North et al., A New Clustering of Antibody CDR Loop Conformations, Journal of Molecular Biology, 406:228-256 (2011)), and Chothia (Chothia C, Lesk A M. Canonical structures for the hypervariable regions of immunoglobulins. J. Mol. Biol. 1987; 196:901-17. Chothia C, Lesk A M, Tramontano A, Levitt M, Smith-Gill S J, Air G, Sheriff S, Padlan E A, Davies D, Tulip W R, et al. Conformations of immunoglobulin hypervariable regions. Nature. 1989; 342:877-83). The CDRs of the antibodies of the present invention are defined according to Table 1.

TABLE 1

CDR numbering conventions used to define the CDRs of the antibodies of the present invention.

| CDR | Starting Amino Acid Residue Defined By: | Ending Amino Acid Residue Defined By: |
|---|---|---|
| HCDR1 | Chothia | Kabat/North |
| HCDR2 | Kabat | Kabat |
| HCDR3 | Chothia/Kabat | Chothia/Kabat |
| LCDR1 | Chothia/Kabat/North | Chothia/Kabat/North |
| LCDR2 | Chothia/Kabat | Chothia/Kabat/North |
| LCDR3 | Chothia/Kabat/North | Chothia/Kabat/North |

The antibodies of the present invention may be prepared and purified using known methods. For example, cDNA sequences encoding a HC (for example the amino acid sequence given by SEQ ID NO: 9) and a LC (for example, the amino acid sequence given by SEQ ID NO: 10) may be cloned and engineered into a GS (glutamine synthetase) expression vector. The engineered immunoglobulin expression vector may then be stably transfected into CHO cells. As one skilled in the art will appreciate, mammalian expression of antibodies will result in glycosylation, typically at highly conserved N-glycosylation sites in the Fc region. Stable clones may be verified for expression of an antibody specifically binding to IL-33. Positive clones may be expanded into serum-free culture medium for antibody production in bioreactors. Medium, into which an antibody has been secreted, may be purified by conventional techniques. For example, the medium may be conveniently applied to a Protein A or G Sepharose FF column that has been equilibrated with a compatible buffer, such as phosphate buffered saline. The column is washed to remove nonspecific binding components. The bound antibody is eluted, for example, by pH gradient and antibody fractions are detected, such as by SDS-PAGE, and then pooled. The antibody may be concentrated and/or sterile filtered using common techniques. Soluble aggregate and multimers may be effectively removed by common techniques, including size exclusion, hydrophobic interaction, ion exchange, or hydroxyapatite chromatography. The product may be immediately frozen, for example at −70° C., or may be lyophilized.

An antibody of the present invention can be incorporated into a pharmaceutical composition which can be prepared by methods well known in the art and comprise an antibody of the present invention and one or more pharmaceutically acceptable carriers, diluents, or excipients.

A pharmaceutical composition comprising an effective amount of an antibody of the present invention can be administered to a patient at risk for, or exhibiting, diseases or disorders as described herein by parental routes (e.g., subcutaneous, intravenous, intraperitoneal, intramuscular, or transdermal). An "effective amount" refers to an amount necessary (at dosages and for periods of time and for the means of administration) to achieve the desired therapeutic result. An effective amount of the antibody may vary according to factors such as the disease state, age, sex, and weight of the individual, and the ability of the antibody to elicit a desired response in the individual. An effective amount is also one in which any toxic or detrimental effects of the antibody of the present invention are outweighed by the therapeutically beneficial effects.

The antibodies of the present invention can be used in the treatment of patients. More particularly the antibodies of the present invention are expected to treat allergic diseases such as atopic dermatitis, asthma, allergic rhinitis, and food allergy. Allergic diseases are a set of chronic conditions involving abnormal immune responses to substances that are ordinarily harmless to most people. The antibodies of the present invention are also expected to treat eosinophilic esophagitis, scleroderma/systemic sclerosis, ulcerative colitis, and chronic obstructive pulmonary disease. The antibodies of the present invention are also expected to treat Crohn's disease.

As used interchangeably herein, "treatment" and/or "treating" and/or "treat" are intended to refer to all processes wherein there may be a slowing, interrupting, arresting, controlling, stopping, or reversing of the progression of the disorders described herein, but does not necessarily indicate a total elimination of all disorder symptoms. Treatment includes administration of an antibody of the present invention for treatment of a disease or condition in a human that would benefit from a reduction in IL-33 activity, and includes: (a) inhibiting further progression of the disease; and (b) relieving the disease, i.e., causing regression of the disease or disorder or alleviating symptoms or complications thereof.

Antibody Engineering

A parental human anti-IL-33 antibody was optimized for binding to human IL-33. To accomplish this, the CDRs of the isolated VH and VL were randomized by mutagenesis and resulting antibodies screened for binding to human IL-33 using an ELISA. Affinity enhancing mutations were then combined to yield Antibody 23, which was then optimized using a framework library approach. For the framework library, twelve human VH framework germline genes (1-24, 1-46, 1-69, 2-5, 3-15, 3-23, 3-53, 3-72, 4-04, 4-39, 5-51, and 6-01) and eight human VL framework genes (A-19, A-26, A-27, B-2, B-3, L-2, L-12, and O-2) containing Antibody 23 CDRs were synthesized and cloned into heavy and light chain human IgG4 expression vectors. Following 293 HEK transient transfection of all 96 heavy and light chain combinations, supernatants were assayed by ELISA for binding to human IL-33 directly coated onto a plate and to biotinylated IL-33 in solution following the capture of Human IgG from supernatants with an anti-human kappa antibody. A human antibody with CDRs derived from antibody Antibody 23, utilizing the 3-53 heavy chain human framework and A27 human light chain framework, was chosen for further development (Antibody 75). The expression of Antibody 75 in transient CHO resulted in higher expression titers as compared to Antibody 23. Furthermore, the purification of Antibody 75 resulted in higher purification yields than Antibody 23. Reduced nonspecific binding to Heparin was also observed with Antibody 75 as compared to Antibody 23. Overall, Antibody 75 had preferred properties compared to Antibody 23. Antibody 75 bound to human IL-33 with an affinity of 14.5 µM and bound to cynomolgus IL-33 with an affinity of 12,400 µM, representing an ~850-fold difference in species cross-reactivity.

Antibody 75 was then optimized for binding to cynomolgus IL-33. To accomplish this, the CDRs of the isolated VH and VL of Antibody 75 were randomized by mutagenesis and resulting antibodies screened for binding to human IL-33 and cynomolgus IL-33 by ELISA. Affinity enhancing mutations to cynomolgus which did not significantly impact affinity to human IL-33 were then combined to yield Antibody 54. Antibody 54 bound to human IL-33 with an affinity of 46 µM and bound to cynomolgus IL-33 with an affinity of 217 µM representing a 5-fold difference in species cross-reactivity. Antibody 54 was then further engineered to reduce potential immunogenicity, which resulted in Antibody 43. Amino acid sequence identification numbers are provided below for Antibodies 43, 54, and 75.

|       | HC       | LC       | HCVR     | LCVR     |
|-------|----------|----------|----------|----------|
| Ab 75 | SEQ ID NO: 1 | SEQ ID NO: 2 | SEQ ID NO: 3 | SEQ ID NO: 4 |
| Ab 54 | SEQ ID NO: 5 | SEQ ID NO: 6 | SEQ ID NO: 7 | SEQ ID NO: 8 |
| Ab 43 | SEQ ID NO: 9 | SEQ ID NO: 10 | SEQ ID NO: 11 | SEQ ID NO: 12 |

EXAMPLES

Example 1: Expression and Purification of Exemplified Antibodies

The antibodies of the invention can be biosynthesized, purified, and formulated for administration by well-known methods. An appropriate host cell, such as HEK 293 or CHO, is either transiently or stably transfected with an expression system for secreting antibodies using a predetermined HC:LC vector ratio if two vectors are used, or a single vector system encoding both heavy chain and light chain. Vectors suitable for expression and secretion of antibodies from these commonly-used host cells are well-known.

Following expression and secretion of the antibody, the medium is clarified to remove cells and the clarified medium is purified using any of many commonly-used techniques. For example, the medium may be applied to a Protein A or G column that has been equilibrated with a buffer, such as phosphate buffered saline (pH 7.4). The column is washed to remove nonspecific binding components. The bound antibody is eluted, for example, by a pH gradient (such as 0.1 M sodium phosphate buffer pH 6.8 to 0.1 M sodium citrate buffer pH 2.5). Antibody fractions are detected, such as by SDS-PAGE, and then are pooled. Further purification is optional, depending on the intended use. The antibody may be concentrated and/or sterile filtered using common techniques. Other materials than the antibody, such as host cell and growth medium components, and soluble aggregates and multimers of the antibody, may be effectively reduced or removed by common techniques, including size exclusion, hydrophobic interaction, cation exchange, anion exchange, affinity, or hydroxyapatite chromatography. The purity of the antibody after these chromatography steps is typically greater than 95%. The product may be frozen at −70° C. or may be lyophilized.

Exemplified Antibody 43 was expressed either transiently in CHO cells after co-transfection of separate heavy chain and light chain expression DNA vectors that incorporated the DNA sequences of SEQ ID NO: 20 and SEQ ID NO: 21, respectively, or was expressed stably in CHO cells after transfection of a single DNA vector that incorporated the DNA sequences of both SEQ ID NO: 20 and SEQ ID NO: 21, which encode the heavy chain and light chain, respectively. Medium harvested from either a 7-day transient CHO culture or a 14-day CHO bulk culture was clarified and the resulting crude supernatant purified by Protein A chromatography. Antibody 43 bound to Protein A resin and was eluted using low pH buffer. The eluted antibody was further purified using either preparative size-exclusion chromatography (SEC), for material produced from transient CHO, or using cation exchange chromatography as a polishing step for material produced from stable CHO. The final purity of Antibody 43 was evaluated by SDS-PAGE, analytical SEC-HPLC, and LC/MS analysis. Endotoxin levels were shown to be <1 EU/mg using Endosafe-PTS analysis. Purified Antibody 43 was stored in PBS (phosphate-buffered saline), pH 7.2 at 4° C.

In Vitro Binding Affinity and Kinetics.

The binding kinetics and affinity of Antibody 43 to human, cynomolgus monkey, mouse, rat, and rabbit IL-33 is determined using a surface plasmon resonance assay on either a Biacore T100 or T200 instrument primed with HBS-EP+ (GE Healthcare, 10 mM Hepes pH7.4, 150 mM NaCl, 3 mM EDTA, 0.05% surfactant P20) running buffer and analysis temperature set at 37° C. A CM4 chip containing immobilized Protein A (generated using standard NHS-EDC amine coupling) on all four flow cells (Fc) is used to employ a capture method. Antibody samples are prepared at 10 µg/mL in running buffer. Mouse, rat, and rabbit IL-33 samples are prepared at final concentrations of 1000, 500, 250, 125, 63, 31, 16, and 0 nM in running buffer. Human and Cynomologus IL-33 samples are prepared at final concentrations of 250, 125, 63, 31, 16, 8, 4, 2, 1, and 0 nM in running buffer. Each analysis cycle involves the steps of (1) capturing antibody samples on separate flow cells (Fc2, Fc3, or Fc4); (2) injecting 200 µL of IL-33 over all flow cells at 100 µL/min; (3) returning to buffer flow for a minimum of 10 min at 100 µL/min to monitor complex dissociation; (4) regenerating the chip surface with two sequential injections of 7.5 microliters of glycine, pH1.5; and (5) equilibrating the chip surface for 5 minutes prior to repeating the cycle. Each IL-33 concentration is injected in duplicate. Data is processed using standard double-referencing and fit to a 1:1 binding model using Biacore T100 Evaluation software, version 2.0.1, to determine the association rate (on-rate, $k_{on}$, $M^{-1}$ $s^{-1}$ units) and the dissociation rate (off-rate, $k_{off}$, $s^{-1}$ units). The equilibrium dissociation constant ($K_D$) is calculated from the relationship $K_D=k_{off}/k_{on}$, and is in molar units.

Three experimental replicates (n) are conducted for the binding of Antibody 43 to human and cynomolgus monkey IL-33.

Following procedures essentially as described above, Antibody 43 had a concentration-dependent binding response to human IL-33 and to cynomolgus monkey IL-33. At the highest concentration of mouse, rat, and rabbit IL-33 injected (1000 nM) the binding response signal did not reach the theoretical half-maximal response signal. As a result, the $K_D$ of Antibody 43 to mouse, rat, and rabbit IL-33 were estimated to be >1000 nM. Similar methods as described above were used to determine the binding kinetics and affinity of Antibody 75 and Antibody 54. Similar methods were also used to determine the binding kinetics and affinity of an anti-IL-33 IgG4 antibody (not of the present invention) having the HCVR and LCVR sequences of APE4909 (disclosed in WO15106080; herein referred to as "Antibody 6"). These results are shown in Table 2.

TABLE 2

IL-33 binding kinetics and affinity of antibodies of the present invention and Antibody 6.

| Antibody | Antigen | $k_{on}$ (M$^{-1}$s$^{-1}$) Avg ± SD | $k_{off}$ (s$^{-1}$) Avg ± SD | $K_D$ (pM) Avg ± SD | N |
|---|---|---|---|---|---|
| Antibody 75* | Human IL-33 | 1.7 ± 0.5 × 10$^6$ | 2.6 ± 0.1 × 10$^{-5}$ | 14.5 ± 1.5 | 3 |
| Antibody 75* | Cynomolgus IL-33 | 1.7 ± 0.6 × 10$^6$ | 1.9 ± 0.1 × 10$^{-2}$ | 12400 ± 4000 | 3 |
| Antibody 54* | Human IL-33 | 1.5 ± 0.5 × 10$^6$ | 6.8 ± 1.3 × 10$^{-5}$ | 46 ± 9 | 3 |
| Antibody 54* | Cynomolgus IL-33 | 1.5 ± 0.2 × 10$^6$ | 3.4 ± 0.5 × 10$^{-4}$ | 217 ± 50 | 3 |
| Antibody 43 | Human IL-33 | 1.5 ± 0.1 × 10$^6$ | 7.2 ± 1.7 × 10$^{-5}$ | 49 ± 14 | 3 |
| Antibody 43 | Cynomolgus IL-33 | 1.5 ± 0.2 × 10$^6$ | 51 ± 2.0 × 10$^{-5}$ | 338 ± 45 | 3 |
| Antibody 6* | Human IL-33 | 1.6 ± 0.1 × 10$^6$ | 4.0 ± 0.9 × 10$^{-4}$ | 252 ± 73 | 2 |
| Antibody 6* | Cynomolgus IL-33 | 1.8 ± 0.6 × 10$^6$ | 1.3 ± 0.1 × 10$^{-3}$ | 804 ± 377 | 2 |
| ntibody 43 | Mouse IL-33 | | | $K_D$ > 1000 nM | 1 |
| Antibody 43 | Rat IL-33 | | | $K_D$ > 1000 nM | 1 |
| Antibody 43 | Rabbit IL-33 | | | $K_D$ > 1000 nM | 1 |

*Tested on different days.

In Vitro Characterization of Binding to Human IL-33 and Other IL-1 Family Members.

BIAcore biosensor 2000 is used to demonstrate the binding specificity of Antibody 43 to human IL-33 and to show that the exemplified antibody does not bind to other members of the human IL-1 protein family.

Protein A (Calbiochem) is coupled via free amine groups to carboxyl groups on flow cells 1 and 2 of a CM5 biosensor chip (GE Healthcare) using a mixture of N-ethyl-N-(dimethylaminopropyl)-carbodiimide (EDC) and N-hydroxysuccinimide (NHS). To capture positive control antibodies, Rabbit anti-Goat IgG (Fc specific) is coupled to flow cell 3, and Rabbit anti-Rat IgG (Fc specific) is coupled to flow cell 4 (both from Jackson ImmunoResearch). Flow cells are monitored with a flow rate of 30 μL/minute using a buffer containing 0.01 M HEPES, pH 7.4, 150 mM NaCl, 0.005% surfactant P20. Antibody 43 is captured on flow cell 2 to yield a total of 300 to 800 response units (RU; results reflect flow cell 2 minus flow cell 1). Binding tests are followed by a regeneration step using glycine-HCl (pH 1.5) between each cycle. Flow cell 1 is used as a control to monitor non-specific binding of analytes tested. The exemplified antibody is tested with all analytes of the human IL-1 protein family as listed at 500 nM concentration.

Following procedures essentially as described above, the results in Table 3 show that Antibody 43 only binds to human IL-33 and not to the other members of the IL-1 family.

TABLE 3

Antibody 43 binds specifically to IL-33.

| Ligand | Exemplified Antibody binding | Positive control binding |
|---|---|---|
| IL-33 | Yes | |
| IL-1α | No | Yes |
| IL-1β | No | Yes |
| IL-1RA | No | Yes |
| IL-18 | No | Yes |
| IL-36α | No | Yes |
| IL-36β | No | Yes |
| IL-36γ | No | Yes |
| IL-36RA | No | Yes |
| IL-37 | No | Yes |

Neutralization of IL-33 in the GEC NFκB-Luciferase Reporter Assay In Vitro.

Human glomerular endothelial cells (GEC) stably transfected with a NFκB-luciferase construct are used to determine the ability of Antibody 43 to inhibit IL-33-induced NFκB activity. The GEC line naturally expresses the ST2 receptor and its co-receptor IL1RAP. In response to human IL-33, the NFκB pathway is activated in GECs.

GEC-NFκB-luc cells are cultured in assay medium (EGM BulletKit medium (LONZA) plus puromycin). On the day prior to the assay, GEC-NFκB-luc cells are plated at 5,000 cells in 50 μl/well in white walled Collagen I treated plates (BD Biocoat), and the plates are incubated overnight.

The next day the cells are treated with Antibody 43 in the presence of IL-33. For each test, 25 μl of exemplified antibody is added per well at a dose range of 0 to 133.3 nM per well. 25 μl of human IL-33 is then added to each well at a final concentration of 126 μM (based on MW=20 kDa). Human monomeric ST2 (IL1RL1) is used as a positive control in the assay in a dose range of 0 to 142.9 nM (final concentration base on MW=35 kDa), and an isotype control antibody is used as a negative control in the assay in a dose range of 0 to 133.3 nM (final concentration base on MW=75 kDa). All samples are run in triplicate. The 96-well plates are incubated at 37° C., 95% relative humidity, 5% $CO_2$ for 4 hours, after which 100 μl/well of One-Glo Luciferase solution is added to measure luciferase activity and plates are read on a luminometer (Perkin Elmer Victor3). The results are shown below in Table 4.

TABLE 4

Exemplified antibody $IC_{50}$ (pM, Avg ± SD) in the in vitro NFκB-GEC-luciferase activity assay.

| Antibody | Human IL-33 $IC_{50}$ | Cyno-IL33 $IC_{50}$ |
|---|---|---|
| Antibody 43 | 330 ± 112 | 1918 ± 152 |
| Antibody 54* | 139 ± 98 | 851 ± 500 |
| Antibody 75* | 286 ± 67 | N.D. |
| Antibody 6* | 292 ± 158 | 1031 |
| Positive control | 426 ± 115 | 175 ± 21 |

*Tested on a different day.

Following procedures essentially as described above, Antibody 43 inhibits human IL-33 and cyno IL-33, but not mouse, rat, or rabbit IL-33-induced NFκB activity in a dose-dependent manner. The average $IC_{50}$ from three independent experiments for human and cyno neutralization is summarized in Table 4. Negative control antibody did not inhibit NFκB activity in GEC-NFκB-luc cells at any concentration tested.

Neutralization of IL-33-Induced GM-CSF Secretion from Human Mast Cells In Vitro.

Inhibition of IL-33-induced GM-CSF release in human mast cells by treatment with Antibody 43 is determined. Human mast cells naturally expressing the ST2 (IL1RL1) receptor and its co-receptor IL1RAP are differentiated in culture from human cord blood stem cells using StemSpan Medium (StemCell) and SCF/IL-6. On the day of the assay, mast cells are plated at 50,000 cells in 50 μl/well in 96-well tissue culture plates in culture medium. Cells are treated with IL-33 in the presence or absence of antibodies. For each test, 25 μl of 4× exemplified antibody is added per well at dose range of 0 to 30 nM. 25 μl of 4× human IL-33 is added to each well to a final concentration 0.5 nM. Assay medium alone is used as a no treatment control and a human monomeric ST2 is used as a positive control at a dose range of 0 to 30 nM. The isotype control antibody tested at 30 nM is used as a negative control. Testing is done in triplicates. The 96-well plates are placed in tissue culture incubator (37° C., 95% relative humidity, 5% $CO_2$) for 16 hours. 100 μl/well of supernatant are collected to measure GM-CSF levels by commercial ELISA (R&D Systems).

Following procedures essentially as described above, Antibody 43 completely inhibited human IL33-induced GM-CSF secretion from human mast cells in a dose-dependent manner, with an $IC_{50}$ of 0.3 nM, which was greater than the positive control soluble receptor $IC_{50}$ of 7.6 nM. In another similar experiment, Antibody 54 inhibited human IL33-induced GM-CSF secretion from human mast cells with an $IC_{50}$ of 0.265 nM, and Antibody 6 inhibited human IL33-induced GM-CSF secretion from human mast cells with an $IC_{50}$ of 0.811 nM. Isotype control antibody did not inhibit IL-33 induced GM-CSF secretion. Results are representative of two independent experiments.

Inhibition of IL-33-Induced IL-5 Production In Vivo.

To confirm neutralization of IL-33 in vivo, to determine whether Antibody 43 is able to neutralize human IL-33 function and inhibit production of mouse IL-5 in vivo, C57BL/6 mice (n=5) are injected intraperitoneally with 0.94 mg/kg, 0.282 mg/kg or 0.094 mg/kg of antibody or with an isotype control antibody at 0.94 mg/kg. One day post-injection, mice are challenged with 0.025 mg/kg of human IL-33 via intraperitoneal injection. Six hours post-human IL-33 challenge, mice are sacrificed and serum is collected. Serum is analyzed for mouse IL-5 production using a commercial ELISA (R&D Systems) as per the manufacturer's instructions.

The results indicated that Antibody 43 is able to completely inhibit the production of mouse IL-5 in a dose dependent manner. The levels of IL-5 in serum of mice injected with 0.94 mg/kg, 0.282 mg/kg or 0.094 mg/kg of exemplified antibody were 0.03±0.004 ng/mL, 0.166±0.036 ng/mL, and 0.430±0.095 ng/mL, respectively. The negative control antibody does not inhibit the human IL-33-induced production of mouse IL-5. These data demonstrate that Antibody 43 inhibits production of mouse IL-5 through neutralization of human IL-33 in vivo.

In Vivo Efficacy of a Surrogate Mouse IL-33 Antibody in an Airway Inflammation Model A surrogate antibody is developed to neutralize mouse IL-33 (mIL-33) for use in preclinical disease models. The surrogate is a murine IgG1 monoclonal antibody that neutralizes mIL-33 in in vitro assays. The ability of systemic administration of the anti-mIL-33 antibody to affect the airway inflammatory response to *Alternaria* challenge is determined in vivo. Female BALB/c mice (n=5 per group) are injected subcutaneously with 25 mg/kg of anti-mIL-33 or isotype control antibody on Day 0. Mouse ST2-Fc, a soluble form of one of the co-receptors for IL-33 that can neutralize mIL-33 in in vitro assays (Positive control), is injected at 12.5 mg/kg intraperitoneally on Days 1 and 2, 30 minutes prior to *Alternaria* administration. *Alternaria* extract (50 μg in 20 μL PBS) is administered intra-nasally to each mouse on days 1 and 2. Mice are sacrificed on day 3 with $CO_2$ inhalation and blood is immediately collected via cardiac puncture for preparation of serum.

Bronchial alveolar lavage fluid (BAL) is prepared by lavaging lungs with 10 washes (500 μL each wash) of PBS injection and withdrawal through a cannula in the exposed trachea of each mouse. BAL fluid is centrifuged at 200 g for 10 minutes and supernatant is removed and frozen. Cells are resuspended in 1 mL ACK buffer (Sigma) to lyse the red blood cells, washed and are resuspended in 0.5 mL of PBS for counting. Eosinophils are counted using eosinophil diluting fluid and stain (ENG Scientific, Cat. ES-3101) and total cells are counted with trypan blue. BAL fluid is assayed using commercial mouse IL-5 and Chitinase 3-like 3/YM1 (Chi3L3/YM1) ELISAs (R&D Systems) and for antibody exposure. The results are shown below in Table 5.

TABLE 5

Levels of IL-5 and Chi3L3/YM1, and number of eosinophils and total number of cells in BAL fluid.

| Cells/Cytokines | Unchallenged | Isotype Control | Anti-mIL-33 | Positive Control |
|---|---|---|---|---|
| Eosinophils (# cells) | 32000 ± 13565 | 340000 ± 70711 | 120000 ± 51769 | 112000 ± 57480 |
| IL-5 (pg/mL) | 2 ± 0 | 69.6 ± 27.31 | 2 ± 0 | 9.2 ± 6.248 |
| Chi3L3/YM1 (ng/mL) | 17.4 ± 2.064 | 108.6 ± 28.7 | 27.4 ± 4.986 | 37.4 ± 6.313 |
| Total Cells (# cells) | 104000 ± 20396 | 408000 ± 95833 | 144000 ± 31241 | 152000 ± 44989 |

Following procedures essentially as described above, *Alternaria* challenge increased the number of cells, mostly eosinophils, present in the BAL fluid. It also induced the production of cytokines such as IL-5 and Chi3L3/YM1. Systemic administration of the anti-mIL-33 antibody significantly reduced eosinophil and total cell infiltration as measured by the BAL cell counts, and decreased IL-5 and Chi3L3/YM1 levels in the BAL fluid. These results demonstrate that inhibition of mIL-33 reduced multiple inflammatory markers in this airway inflammation model.

Epitope Mapping by X-Ray Crystallography

X-Ray Crystallography

A 10.6 mg/ml solution of hIL33:FAB complex is screened for crystals utilizing custom and commercially available screens. Vapor diffusion experiments are set up at 22° C. as 400 nL+400 nL (protein+well solution) crystallization drops with 50 µL well solution (0.2 M Ammonium Sulfate and 30% w/v Polyethylene Glycol 8,000) in a MRC2 (SWISSCI) sitting drop plate. 20 mM Magnesium Acetate is added to the protein to aid in crystallization. Resulting crystals are flash frozen in liquid nitrogen following a quick dip in well solution containing 20% Ethylene Glycol added as a cryogenic agent. X-ray diffraction data are collected using synchrotron radiation at LRL-CAT 31-ID (Advanced Photon Source, Argonne, Ill.). 180 frames are collected at 1° oscillation at a wavelength of 0.97931 Å and processed with CCP41 packages.

The crystals are of the P21212 space group with unit cell dimensions a=70.1 Å b=194.9 Å c=46.5 Å α=β=γ=90°. A molecular replacement solution of the hIL33:FAB complex is obtained with Phaser2 using input models from PDB structure 4KC3 and a FAB model generated with the MOE3 (v2014.9) antibody modeling tool. The molecular replacement solution contains 1 complex in the asymmetric unit. This solution subsequently undergoes multiple rounds of refinement and model building with Buster4 and Coot5 yielding a final structure with Rwork of 17.8% and Rfree of 20.3% at 1.40 Å.

The hIL33 epitope is mapped for the high resolution crystal structure of hIL33:FAB complex using the Protein Contacts tool in MOE3 (v2015.10). The tool is used to evaluate "distance", "covalent", "arene", "ionic", and "hbond" interactions. The output for the interchain interactions is distilled down to the residue level in Microsoft Excel to identify the hIL33 epitope residues. The final list contains hIL33 residues that are within 4.5 Å of any FAB residue.

Following procedure essentially as described above, an antibody having the same CDRs as Antibody 75 contacts human IL-33 at an epitope given by the following residues of SEQ ID NO: 19: Ser at position 23; Pro at position 24; Ile at position 25; Thr at position 26; Glu at position 27; Tyr at position 28; Leu at position 29; Tyr at position 69; Glu at position 71; Val at position 83; Asp at position 84; Lys at position 86; Leu at position 88; Leu at position 126; Asn at position 128; Met at position 129; Asn at position 132; Cys at position 133; Val at position 134; Glu at position 175; and Thr at position 176. Antibody 54 and Antibody 43 also contact a substantially similar epitope on human IL-33.

---

Sequences

HC of Antibody 75 (SEQ ID NO: 1)
EVQLVETGGGLIQPGGSLRLSCAASGFTFSSYAMSWVRQAPGKGLEWVSA
ISGSGGSTYYADSVKGRFTISRDNSKNTLYLQMNSLRAEDTAVYYCARTL
HGIRAAYDAFIIWGQGTLVTVSSASTKGPSVFPLAPCSRSTSESTAALGC
LVKDYFPEPVTVSWNSGALTSGVHTFPAVLQSSGLYSLSSVVTVPSSSLG
TKTYTCNVDHKPSNTKVDKRVESKYGPPCPPCPAPEAAGGPSVFLFPPKP
KDTLMISRTPEVTCVVVDVSQEDPEVQFNWYVDGVEVHNAKTKPREEQFN
STYRVVSVLTVLHQDWLNGKEYKCKVSNKGLPSSIEKTISKAKGQPREPQ
VYTLPPSQEEMTKNQVSLTCLVKGFYPSDIAVEWESNGQPENNYKTTPPV
LDSDGSFFLYSRLTVDKSRWQEGNVFSCSVMHEALHNHYTQKSLSLSLG LC of Antibody 75 (SEQ ID NO: 2)
EIVLTQSPGTLSLSPGERATLSCRASQSVGINLSWYQQKPGQAPRLLIYG
ASHRATGIPDRFSGSGSGTDFTLTISRLEPEDFAVYYCHQYSQSPPFTFG
GGTKVEIKRTVAAPSVFIFPPSDEQLKSGTASVVCLLNNFYPREAKVQWK
VDNALQSGNSQESVTEQDSKDSTYSLSSTLTLSKADYEKHKVYACEVTHQ
GLSSPVTKSFNRGEC HCVR of Antibody 75 (SEQ ID NO: 3)
EVQLVETGGGLIQPGGSLRLSCAASGFTFSSYAMSWVRQAPGKGLEWVSA
ISGSGGSTYYADSVKGRFTISRDNSKNTLYLQMNSLRAEDTAVYYCARTL
HGIRAAYDAFIIWGQGTLVTVSS LCVR of Antibody 75 (SEQ ID NO: 4)
EIVLTQSPGTLSLSPGERATLSCRASQSVGINLSWYQQKPGQAPRLLIYG
ASHRATGIPDRFSGSGSGTDFTLTISRLEPEDFAVYYCHQYSQSPPFTFG
GGTKVEIK HC of Antibody 54 (SEQ ID NO: 5)
EVQLVETGGGLIQPGGSLRLSCAASGFTFSFYAMSWVRQAPGKGLEWVSA
ISGSGGSTYYADSVKGRFTISRDNSKNTLYLQMNSLRAEDTAVYYCARTL
HGIRAAYDAFIIWGQGTLVTVSSASTKGPSVFPLAPCSRSTSESTAALGC
LVKDYFPEPVTVSWNSGALTSGVHTFPAVLQSSGLYSLSSVVTVPSSSLG
TKTYTCNVDHKPSNTKVDKRVESKYGPPCPPCPAPEAAGGPSVFLEPPKP
KDTLMISRTPEVTCVVVDVSQEDPEVQFNWYVDGVEVHNAKTKPREEQFN
STYRVVSVLTVLHQDWLNGKEYKCKVSNKGLPSSIEKTISKAKGQPREPQ
VYTLPPSQEEMTKNQVSLTCLVKGFYPSDIAVEWESNGQPENNYKTTPPV
LDSDGSFFLYSRLTVDKSRWQEGNVFSCSVMHEALHNHYTQKSLSLSLG LC of Antibody 54 (SEQ ID NO: 6)
EIVLTQSPGTLSLSPGERATLSCRASQSVGINLSWYQQKPGQAPRLLIYG
ASHRLTGIPDRFSGSGSGTDFTLTISRLEPEDFAVYYCHQYSQPPPFTFG
GGTKVEIKRTVAAPSVFIFPPSDEQLKSGTASVVCLLNNFYPREAKVQWK
VDNALQSGNSQESVTEQDSKDSTYSLSSTLTLSKADYEKHKVYACEVTHQ
GLSSPVTKSFNRGEC HCVR of Antibody 54 (SEQ ID NO: 7)
EVQLVETGGGLIQPGGSLRLSCAASGFTFSFYAMSWVRQAPGKGLEWVSA
ISGSGGSTYYADSVKGRFTISRDNSKNTLYLQMNSLRAEDTAVYYCARTL
HGIRAAYDAFIIWGQGTLVTVSS LCVR of Antibody 54 (SEQ ID NO: 8)
EIVLTQSPGTLSLSPGERATLSCRASQSVGINLSWYQQKPGQAPRLLIYG
ASHRLTGIPDRFSGSGSGTDFTLTISRLEPEDFAVYYCHQYSQPPPFTFG
GGTKVEIK HC of Antibody 43 (SEQ ID NO: 9)
EVQLVETGGGLIQPGGSLRLSCAASGFTFSFYAMSWVRQAPGKGLEWVSA
ISGSGGSTYYADSVKGRFTISRDNSKNTLYLQMNSLRAEDTAVYYCARTI
EGIRAAYDAFIIWGQGTLVTVSSASTKGPSVFPLAPCSRSTSESTAALGC
LVKDYFPEPVTVSWNSGALTSGVHTFPAVLQSSGLYSLSSVVTVPSSSLG
TKTYTCNVDHKPSNTKVDKRVESKYGPPCPPCPAPEAAGGPSVFLEPPKP
KDTLMISRTPEVTCVVVDVSQEDPEVQFNWYVDGVEVHNAKTKPREEQFN
STYRVVSVLTVLHQDWLNGKEYKCKVSNKGLPSSIEKTISKAKGQPREPQ
VYTLPPSQEEMTKNQVSLTCLVKGFYPSDIAVEWESNGQPENNYKTTPPV
LDSDGSFFLYSRLTVDKSRWQEGNVFSCSVMHEALHNHYTQKSLSLSLG LC of Antibody 43 (SEQ ID NO: 10)
EIVLTQSPGTLSLSPGERATLSCRASQSVGINLSWYQQKPGQAPRLLIYG
ASHRLTGIPDRFSGSGSGTDFTLTISRLEPEDFAVYYCHQYSQPPPFTFG
GGTKVEIKRTVAAPSVFIFPPSDEQLKSGTASVVCLLNNFYPREAKVQWK
VDNALQSGNSQESVTEQDSKDSTYSLSSTLTLSKADYEKHKVYACEVTHQ
GLSSPVTKSFNRGEC HCVR of Antibody 43 (SEQ ID NO: 11)
EVQLVETGGGLIQPGGSLRLSCAASGFTFSFYAMSWVRQAPGKGLEWVSA
ISGSGGSTYYADSVKGRFTISRDNSKNTLYLQMNSLRAEDTAVYYCARTI
FIGIRAAYDAFIIWGQGTLVTVSS LCVR of Antibody 43 (SEQ ID NO: 12)
EIVLTQSPGTLSLSPGERATLSCRASQSVGINLSWYQQKPGQAPRLLIYG
ASHRLTGIPDRFSGSGSGTDFTLTISRLEPEDFAVYYCHQYSQPPPFTFG
GGTKVEIK HCDR1 (SEQ ID NO: 13)
GFTFSXYAMS
Wherein X at position 6 is S or F.

HCDR2 (SEQ ID NO: 14)
AISGSGGSTYYADSVKG

HCDR3 (SEQ ID NO: 15)
TXHGIRAAYDAFII
Wherein X at position 2 is L or I.

| Sequences |
|---|
| LCDR1 (SEQ ID NO: 16)<br>RASQSVGINLS<br><br>LCDR2 (SEQ ID NO: 17)<br>GASHRXT<br>Wherein X at position 6 is A or L.<br><br>LCDR3 (SEQ ID NO: 18)<br>HQYSQXPPFT<br>Wherein X at position 6 is S or P.<br><br>Human IL-33 Amino Acids 95-270 (SEQ ID NO: 19)<br>AFGISGVQKYTRALHDSSITGISPITEYLASLSTYNDQSITFALEDESYE<br>IYVEDLKKDEKKDKVLLSYYESQHPSNESGDGVDGKMLMVTLSPTKDFWL<br>HANNKEHSVELHKCEKPLPDQAFFVLHNMHSNCVSFECKTDPGVFIGVKD<br>NHLALIKVDSSENLCTENILFKLSET<br><br>DNA Encoding the HC of SEQ ID NO: 9 (SEQ ID NO: 20)<br>GAGGTGCAGCTGGTGGAGACTGGAGGAGGCTTGATCCAGCCTGGGGGGTC<br>CCTGAGACTCTCCTGTGCAGCCTCTGGATTCACCTTTAGCTTTTATGCTA<br>TGAGCTGGGTCCGCCAGGCTCCAGGGAAGGGGCTGGAGTGGGTCTCAGCT<br>ATTAGTGGTAGTGGTGGTAGCACATACTACGCAGATTCCGTGAAGGGCCG<br>ATTCACCATCTCCAGAGACAATTCCAAGAACACGCTGTATCTTCAAATGA<br>ACAGCCTGAGAGCCGAGGACACGGCCGTGTATTACTGTGCGAGAACGATC<br>CACGGTATACGCGCAGCCTATGATGCTTTTATTATCTGGGGCCAGGGCAC<br>CCTGGTCACCGTCTCCTCAGCTTCTACCAAGGGCCCATCGGTCTTCCCGC<br>TAGCGCCCTGCTCCAGGAGCACCTCCGAGAGCACAGCGCCCTGGGCTGC<br>CTGGTCAAGGACTACTTCCCCGAACCGGTGACGGTGTCGTGGAACTCAGG<br>CGCCCTGACCAGCGGCGTGCACACCTTCCCGGCTGTCCTACAGTCCTCAG<br>GACTCTACTCCCTCAGCAGCGTGGTGACCGTGCCCTCCAGCAGCTTGGGC<br>ACGAAGACCTACACCTGCAACGTAGATCACAAGCCCAGCAACACCAAGGT |
| GGACAAGAGAGTTGAGTCCAAATATGGTCCCCCATGCCCACCCTGCCCAG<br>CACCTGAGGCCGCCGGGGGACCATCAGTCTTCCTGTTCCCCCCAAAACCC<br>AAGGACACTCTCATGATCTCCCGGACCCCTGAGGTCACGTGCGTGGTGGT<br>GGACGTGAGCCAGGAAGACCCCGAGGTCCAGTTCAACTGGTACGTGGATG<br>GCGTGGAGGTGCATAATGCCAAGACAAAGCCGCGGGAGGAGCAGTTCAAC<br>AGCACGTACCGTGTGGTCAGCGTCCTCACCGTCCTGCACCAGGACTGGCT<br>GAACGGCAAGGAGTACAAGTGCAAGGTCTCCAACAAAGGCCTCCCGTCCT<br>CCATCGAGAAAACCATCTCCAAAGCCAAAGGGCAGCCCCGAGAGCCACAG<br>GTGTACACCCTGCCCCCATCCCAGGAGGAGATGACCAAGAACCAGGTCAG<br>CCTGACCTGCCTGGTCAAAGGCTTCTACCCCAGCGACATCGCCGTGGAGT<br>GGGAGAGCAATGGGCAGCCGGAGAACAACTACAAGACCACGCCTCCCGTG<br>CTGGACTCCGACGGCTCCTTCTTCCTCTACAGCAGGCTAACCGTGGACAA<br>GAGCAGGTGGCAGGAGGGGAATGTCTTCTCATGCTCCGTGATGCATGAGG<br>CTCTGCACAACCACTACACACAGAAGAGCCTCTCCCTGTCTCTGGGT<br><br>DNA Encoding the LC of SEQ ID NO: 10 (SEQ ID NO: 21)<br>GAAATTGTGTTGACGCAGTCTCCAGGCACCCTGTCTTTGTCTCCAGGGGA<br>AAGAGCCACCCTCTCCTGCAGGGCCAGTCAGAGTGTTGGCATCAACTTGT<br>CCTGGTACCAGCAGAAACCTGGCCAGGCTCCCAGGCTCCTCATCTATGGT<br>GCATCCCATAGGCTAACTGGCATCCCAGACAGGTTCAGTGGCAGTGGGTC<br>TGGGACAGACTTCACTCTCACCATCAGCAGACTGGAGCCTGAAGATTTTG<br>CAGTGTATTACTGTCATCAATATAGTCAACCACCTCCCTTCACTTTCGGC<br>GGAGGGACCAAGGTGGAGATCAAACGGACCGTGGCTGCACCATCTGTCTT<br>CATCTTCCCGCCATCTGATGAGCAGTTGAAATCTGGAACTGCCTCTGTTG<br>TGTGCCTGCTGAATAACTTCTATCCCAGAGAGGCCAAAGTACAGTGGAAG<br>GTGGATAACGCCCTCCAATCGGGTAACTCCCAGGAGAGTGTCACAGAGCA<br>GGACAGCAAGGACAGCACCTACAGCCTCAGCAGCACCCTGACGCTGAGCA<br>AAGCAGACTACGAGAAACACAAAGTCTACGCCTGCGAAGTCACCCATCAG<br>GGCCTGAGCTCGCCCGTCACAAAGAGCTTCAACAGGGGAGAGTGC |

We claim:

1. An antibody that binds human IL-33, comprising a light chain variable region (LCVR) and a heavy chain variable region (HCVR), wherein the LCVR comprises complementarity determining regions (CDRs) LCDR1, LCDR2, and LCDR3 and the HCVR comprises CDRs HCDR1, HCDR2, and HCDR3, and wherein the amino acid sequence of LCDR1 is SEQ ID NO: 16, the amino acid sequence of LCDR2 is SEQ ID NO: 17, the amino acid sequence of LCDR3 is SEQ ID NO: 18, the amino acid sequence of HCDR1 is SEQ ID NO: 13, the amino acid sequence of HCDR2 is SEQ ID NO: 14, and the amino acid sequence of HCDR3 is SEQ ID NO: 15, and wherein Xaa at position 6 of SEQ ID NO: 13 is Ser or Phe, Xaa at position 2 of SEQ ID NO: 15 is Leu or Ile, Xaa at position 6 of SEQ ID NO: 17 is Ala or Leu, and Xaa at position 6 of SEQ ID NO: 18 is Ser or Pro.

2. The antibody of claim 1, wherein:
a. Xaa at position 6 of SEQ ID NO: 13 is Ser;
b. Xaa at position 2 of SEQ ID NO: 15 is Leu;
c. Xaa at position 6 of SEQ ID NO: 17 is Ala; and
d. Xaa at position 6 of SEQ ID NO: 18 is Ser.

3. The antibody of claim 1, wherein:
a. Xaa at position 6 of SEQ ID NO: 13 is Phe;
b. Xaa at position 2 of SEQ ID NO: 15 is Leu;
c. Xaa at position 6 of SEQ ID NO: 17 is Leu; and
d. Xaa at position 6 of SEQ ID NO: 18 is Pro.

4. The antibody of claim 1, wherein:
a. Xaa at position 6 of SEQ ID NO: 13 is Phe;
b. Xaa at position 2 of SEQ ID NO: 15 is Ile;
c. Xaa at position 6 of SEQ ID NO: 17 is Leu; and
d. Xaa at position 6 of SEQ ID NO: 18 is Pro.

5. The antibody of claim 1, wherein the amino acid sequence of the LCVR is SEQ ID NO: 4, SEQ ID NO: 8, or SEQ ID NO: 12, and the amino acid sequence of the HCVR is SEQ ID NO: 3, SEQ ID NO: 7, or SEQ ID NO: 11.

6. The antibody of claim 5, wherein the amino acid sequence of the LCVR is SEQ ID NO: 4, and the amino acid sequence of the HCVR is SEQ ID NO: 3.

7. The antibody of claim 5, wherein the amino acid sequence of the LCVR is SEQ ID NO: 8, and the amino acid sequence of the HCVR is SEQ ID NO: 7.

8. The antibody of claim 5, wherein the amino acid sequence of the LCVR is SEQ ID NO: 12, and the amino acid sequence of the HCVR is SEQ ID NO: 11.

9. The antibody of claim 1, wherein the antibody comprises a light chain (LC) and a heavy chain (HC), and wherein the amino acid sequence of the LC is SEQ ID NO: 2, SEQ ID NO: 6, or SEQ ID NO: 10, and the amino acid sequence of the HC is SEQ ID NO: 1, SEQ ID NO: 5, or SEQ ID NO: 9.

10. The antibody of claim 9, wherein the amino acid sequence of the LC is SEQ ID NO: 2, and the amino acid sequence of the HC is SEQ ID NO: 1.

11. The antibody of claim 9, wherein the amino acid sequence of the LC is SEQ ID NO: 6, and the amino acid sequence of the HC is SEQ ID NO: 5.

12. The antibody of claim 9, wherein the amino acid sequence of the LC is SEQ ID NO: 10, and the amino acid sequence of the HC is SEQ ID NO: 9.

13. A pharmaceutical composition comprising the antibody of claim 1, and one or more pharmaceutically acceptable carriers, diluents, or excipients.

14. A method of treating one or more allergic disease, comprising administering to a patient in need thereof an effective amount of the antibody of claim 1.

15. The method of claim 14, wherein the allergic disease is atopic dermatitis, asthma, allergic rhinitis, or food allergy.

16. A method of treating atopic dermatitis, comprising administering to a patient in need thereof an effective amount of the antibody of claim 1.

17. A method of treating at least one of eosinophilic esophagitis, scleroderma/systemic sclerosis, ulcerative colitis, and chronic obstructive pulmonary disease, comprising administering to a patient in need thereof an effective amount of the antibody of claim 1.

* * * * *

UNITED STATES PATENT AND TRADEMARK OFFICE
CERTIFICATE OF CORRECTION

PATENT NO. : 10,501,536 B2 Page 1 of 1
APPLICATION NO. : 15/791641
DATED : October 24, 2017
INVENTOR(S) : Robert Jan Benschop et al.

It is certified that error appears in the above-identified patent and that said Letters Patent is hereby corrected as shown below:

On the Title Page

Please use the following title:
ANTI-IL-33 ANTIBODIES AND USES THEREOF

Signed and Sealed this
Second Day of March, 2021

Drew Hirshfeld
*Performing the Functions and Duties of the*
*Under Secretary of Commerce for Intellectual Property and*
*Director of the United States Patent and Trademark Office*